US00PP30327P3

(12) United States Plant Patent
Pineau

(10) Patent No.: US PP30,327 P3
(45) Date of Patent: Apr. 2, 2019

(54) ***COTINUS* PLANT NAMED 'MINCOJAU3'**

(50) Latin Name: *Cotinus coggygria*
Varietal Denomination: MINCOJAU3

(71) Applicant: Patrick Pineau, Saint Mathurin sur Loire (FR)

(72) Inventor: Patrick Pineau, Saint Mathurin sur Loire (FR)

(73) Assignee: Hortival Diffusion SAS (FR)

( * ) Notice: Subject to any disclaimer, the term of this patent is extended or adjusted under 35 U.S.C. 154(b) by 0 days.

(21) Appl. No.: 15/731,532

(22) Filed: Jun. 22, 2017

(65) Prior Publication Data

US 2018/0376642 P1 Dec. 27, 2018

(51) Int. Cl.
*A01H 5/00* (2018.01)
*A01H 6/00* (2018.01)
*A01H 5/12* (2018.01)

(52) U.S. Cl.
USPC ..... Plt./226
CPC ..... *A01H 6/00* (2018.05); *A01H 5/12* (2013.01)

(58) Field of Classification Search
USPC ..... Plt./226
CPC ..... A01H 5/02; A01H 5/00; A01H 5/12
See application file for complete search history.

(56) References Cited

PUBLICATIONS

GTITM UPOVROM Citation for 'Mincojau3' as per QZ PBR 20151714; Jul. 21, 2015; 1 page.*

* cited by examiner

*Primary Examiner* — Kent L Bell
(74) *Attorney, Agent, or Firm* — Cassandra Bright

(57) ABSTRACT

A new and distinct *Cotinus* cultivar named 'MINCOJAU3' is disclosed, characterized by distinctively yellow foliage which resists sun scorching and does not turn entirely green during Summer. Plants are of medium size, vigorous, compact and rounded in form. The new variety is a *Cotinus*, normally produced as an outdoor garden or container plant.

3 Drawing Sheets

Latin name of the genus and species: *Cotinus coggygria*. Variety denomination: 'MINCOJAU3'.

BACKGROUND OF THE INVENTION

The new *Cotinus* cultivar is a product of a planned breeding program conducted by the inventor in La Menitre, France. The objective of the breeding program was to produce new *Cotinus coggygria* varieties having yellow foliage and compact habits for container production. The crossing resulting in this new variety was made during 2005.

The seed parent is *Cotinus coggygria* 'Ancot', unpatented, the pollen parent is *Cotinus coggygria* 'Royal Purple', unpatented. The new variety was identified as a potentially interesting selection during 2009. Selection was made at a research nursery in La Menitre, France.

Asexual reproduction of the new cultivar 'MINCOJAU3' was first performed in 2009 at a commercial nursery in La Menitre, France. Vegetative soft wood cuttings were used. Subsequent propagation has shown that the unique features of this cultivar are stable and reproduced true to type in successive generations.

SUMMARY OF THE INVENTION

The cultivar 'MINCOJAU3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINCOJAU3' These characteristics in combination distinguish 'MINCOJAU3' as a new and distinct *Cotinus* cultivar:

1. Compacted, rounded plant form.
2. Yellow foliage with Greyed-Orange new leaves in Spring.
3. Medium sized plants.
4. Foliage resists sun damage.

PARENT COMPARISON

Plants of the new cultivar 'MINCOJAU3' are similar to plants of the seed parent variety in most horticultural characteristics, however, plants of the new cultivar 'MINCOJAU3' differ in the following;

1. The new variety has a more rounded plant habit, the seed parent is upright.
2. New foliage of 'MINCOJAU3' is yellow and Greyed-Orange, new foliage of 'Ancot' is yellow and light red.
3. Summer foliage of the new variety is bright yellow, summer foliage of the seed parent is light yellow.
4. Foliage shape of the new variety is obovate, foliage shape of 'Ancot' is oblong.
5. The new variety is more vigorous than the seed parent.

Plants of the new cultivar 'MINCOJAU3' are similar to plants of the pollen parent variety in most horticultural characteristics, however, plants of the new cultivar 'MINCOJAU3' differ in the following;

1. The new variety has yellow foliage, the pollen parent has deep burgundy foliage.

COMMERCIAL COMPARISON

At the time of filing, other yellow foliage *Cotinus* were not known for comparison. However, plants of the new cultivar 'MINCOJAU3' can be compared to the variety *Cotinus* 'Grace'. These varieties are similar in most horticultural characteristics however, 'MINCOJAU3' differs in the following:

1. The new variety has yellow foliage, 'Grace' has somewhat greyed-orange foliage, during, deep burgundy in the Fall.

BRIEF DESCRIPTION OF THE PHOTOGRAPHS

The accompanying photograph in FIG. 1 illustrates in full color a typical mature plant of 'MINCOJAU3' grown outdoors, at approximately 5 years old.

DETAILED BOTANICAL DESCRIPTION

Figure 1:
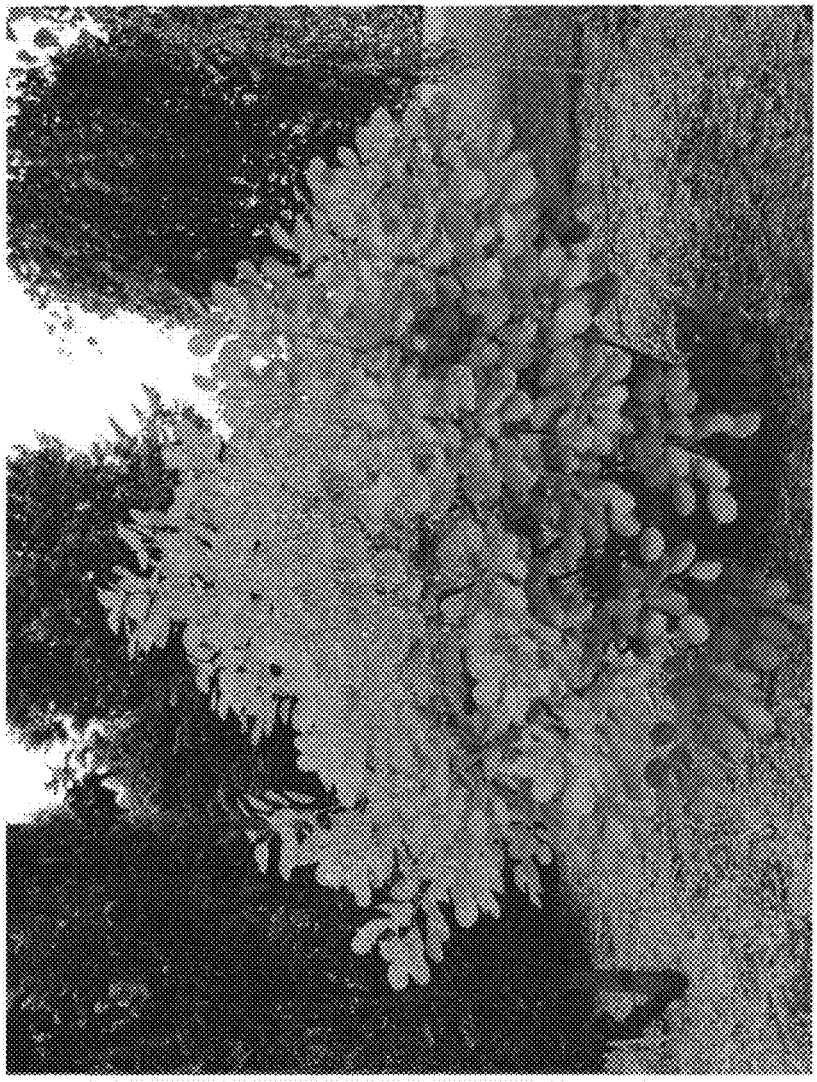
Figure 2:
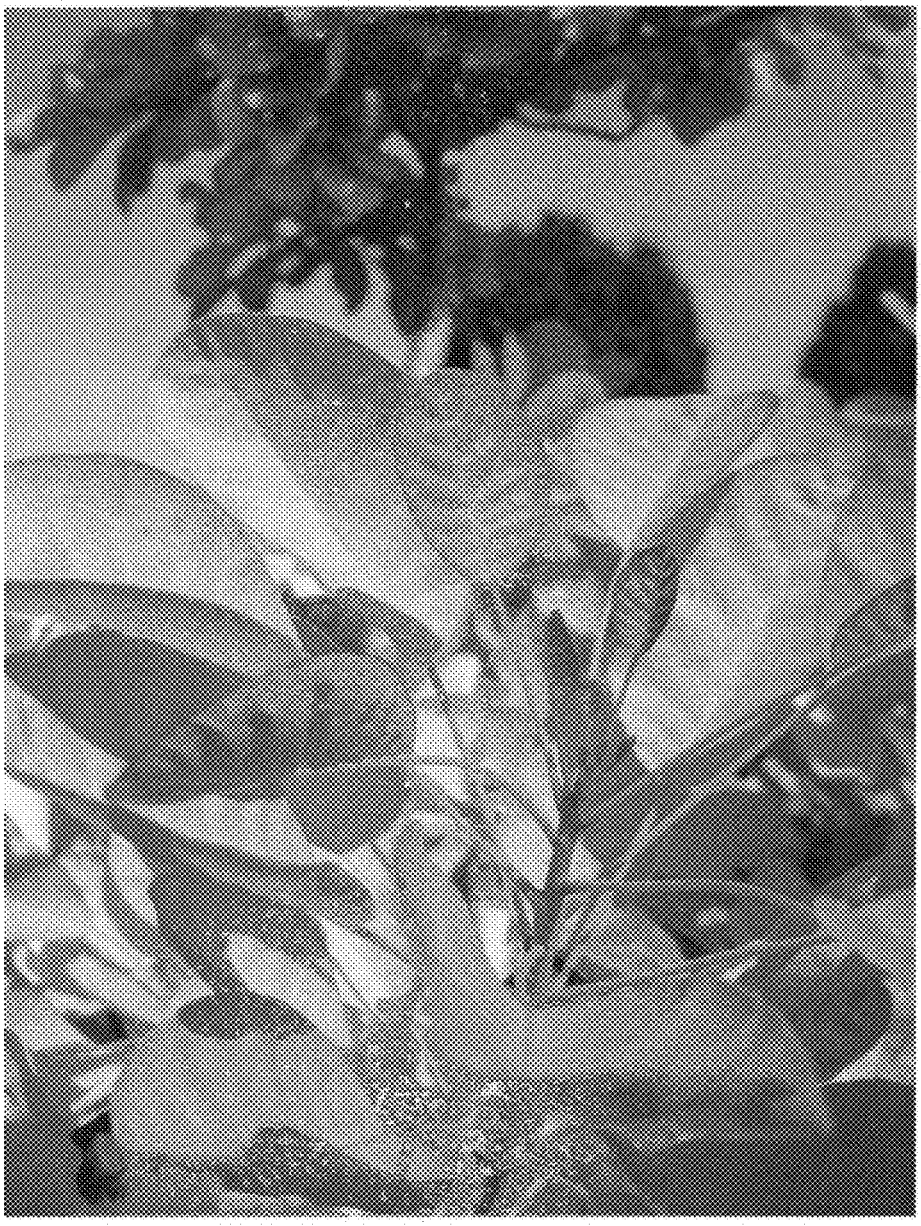
FIG. 2 illustrates a closeup view of the foliage, including new Spring growth.
Figure 3:
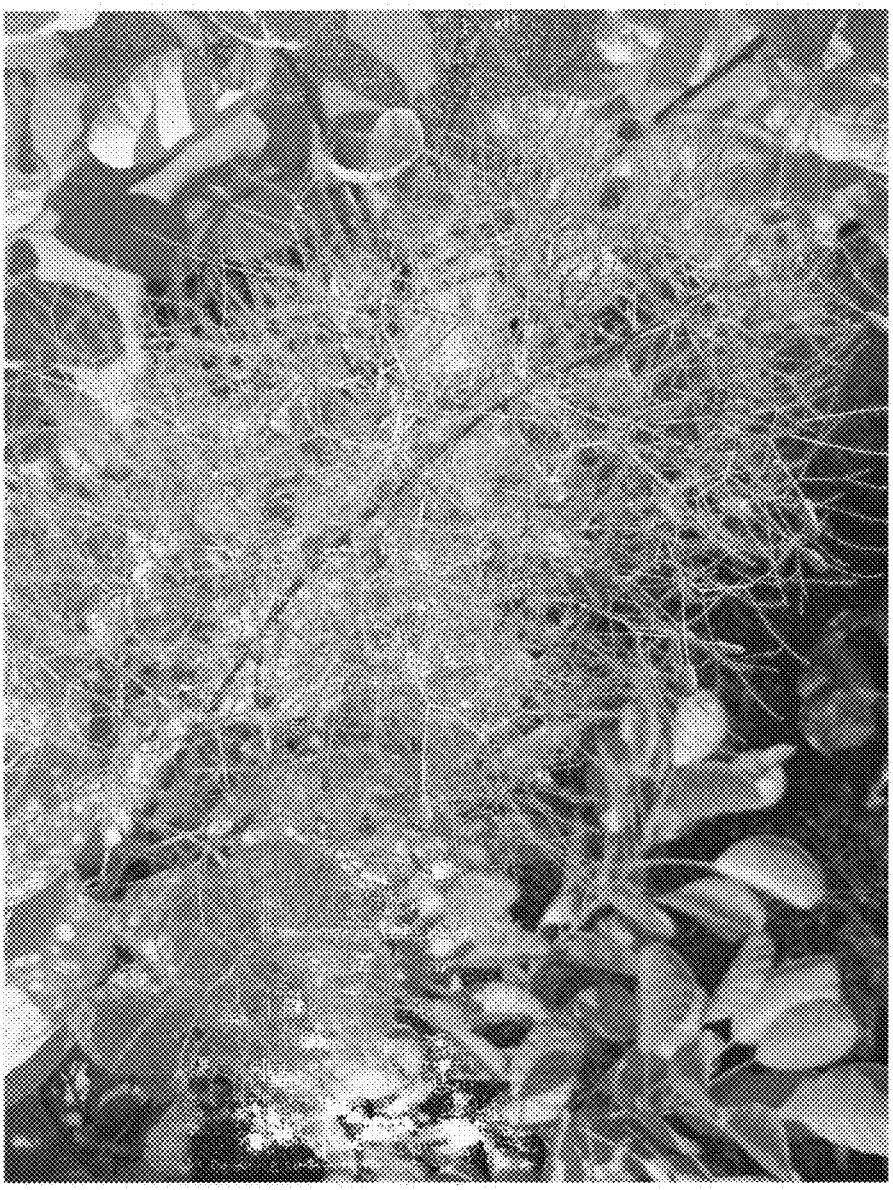
FIG. 3 illustrates in full color a typical inflorescence of 'MINCOJAU3'. The photographs were taken using conventional techniques and although colors may appear different from actual colors due to light reflectance it is as accurate as possible by conventional photographic techniques.

In the following description, color references are made to The Royal Horticultural Society Colour Chart 2015, $6^{th}$ edition, except where general terms of ordinary dictionary significance are used. The following observations and measurements describe 'MINCOJAU3' plants grown in a polyhouse in Grand Haven, Mich. Measurements were taken during May. The plants were about 2 years old in 5 gallon containers. The growing temperature ranged from approximately 18° C. to 27° C. during the day and 5° C. to 10° C. at night. Measurements and numerical values represent averages of typical plant types.

Botanical classification: *Cotinus coggygria* 'MINCOJAU3'.

PROPAGATION

Time to initiate roots: 20 days at approximately 25° C.

Root description: Fibrous, medium root thickness. Tan/brown in color, not effectively measured with a color chart.

Time to produce a rooted young plant: About 90 days at 25° C.

PLANT

Plant type: Perennial shrub.

Age of plant described: Approximately 2 years old.

Growth habit: Upright, rounded.

Pot size of plant described: 5 gallon pot.

Overall plant shape: Globular upright.

Height: 200 cm.

Plant spread: 200 cm.

Plant vigor: Strong.

Branching characteristics: Upright and compact. Basal and lateral branching. Pinching not required.

Length of primary lateral branches: Average 150 cm.

Diameter of lateral branches: 5 mm.

Quantity of lateral branches: Average 12.

Stem:

- *Stem shape.*—Round.
- *Stem strength.*—Flexible.
- *Color.*—Stem: Near RHS Greyed-Orange 164A.
- *Texture.*—Glabrous.
- *Angle of attachment.*—0 to 20 degrees from center of plant.

Internode length: 2 cm on average.

FOLIAGE

Leaf:

- *Arrangement.*—Alternate, single.
- *Leaves per branch.*—Average range 20 to 60, depending upon length of branch.
- *Leaf shape.*—Obovate.
- *Length.*—8.0 cm.
- *Width.*—6.2 cm.
- *Apex.*—Acute.
- *Base.*—Cuneate.
- *Margin.*—Entire.
- *Texture of top surface.*—Smooth.
- *Texture of bottom surface.*—Smooth, with noticeable veins.
- *Color.*—Young foliage upper side: Near RHS Yellow 9A, flushed Greyed-Orange 172B, margin 172A. Interior has a lighter flush, near 172D. Young foliage under side: Near RHS Yellow 9A, flushed Greyed-Orange 172B, margin 172A. Interior has a lighter flush, near 172D. Mature foliage upper side: Near RHS Yellow 13B. Mature foliage under side: Near RHS Yellow 13B.
- *Venation.*—Pattern: Palmate. Color upper side: Near RHS Yellow-Green 144C. Color under side: Near RHS Yellow-Green 144C.
- *Petiole.*—Average Length: 18 mm. Diameter: 1 mm. Petiole color upper side: Near RHS Greyed-Orange N170A. Petiole color lower side: Near RHS Greyed-Orange 164A. Petiole Texture upper side: Smooth. Petiole Texture lower side: Smooth.

FLOWER

Inflorescence:

- *Type.*—Panicle.
- *Length/height.*—28 cm.
- *Width.*—20 cm.

Flower:

- *Type.*—Single.
- *Diameter.*—5 mm.
- *Height.*—2 mm.
- *Persistent or self-cleaning.*—Self-cleaning.
- *Fragrance.*—None detected.

Petal:

- *Number.*—4-5.
- *Fused.*—Not fused.
- *Base.*—Rounded.
- *Shape.*—Ovate.
- *Margin.*—Entire.
- *Apex.*—Acute.
- *Length.*—2 mm.
- *Width.*—1.5 mm.
- *Color.*—When opening, upper side: Yellow-Green 150D. Fully opened, upper side: Yellow-Green 150D.
- *Petaloids.*—Absent.

Sepal:

*Number.*—4-5.

*Shape.*—Ovate.

*Margin.*—Entire.

*Length.*—0.2 mm.

*Width.*—0.1 mm.

*Color.*—Yellow-Green 144C.

OTHER CHARACTERISTICS

Flower: Pink red silky hairs on flowerless pedicel.

Seeds and fruits:

*Fruit type.*—Reniform drupe.

*Fruit length.*—0.5 cm.

*Fruit diameter.*—0.4 cm.

*Fruit color.*—Yellow-Green 144A, then green and pink.

*Seed number.*—1 seed per flower.

Disease/pest resistance: Neither resistance nor susceptibility to normal diseases and pests of *Cotinus coggygria* have been observed.

Garden performance: Good tolerance, performs well in humid conditions.

Temperature tolerance: Typical range USDA zones 4 through 9.

What is claimed is:

1. A new and distinct cultivar of *Cotinus* plant named 'MINCOJAU3' as herein illustrated and described.

* * * * *